(12) United States Patent
Matoba

(10) Patent No.: US 8,912,503 B2
(45) Date of Patent: Dec. 16, 2014

(54) TRANSMISSION X-RAY ANALYZER AND TRANSMISSION X-RAY ANALYSIS METHOD

(75) Inventor: Yoshiki Matoba, Chiba (JP)

(73) Assignee: SII NanoTechnology Inc. (JP)

( * ) Notice: Subject to any disclaimer, the term of this patent is extended or adjusted under 35 U.S.C. 154(b) by 0 days.

(21) Appl. No.: 13/564,802

(22) Filed: Aug. 2, 2012

(65) Prior Publication Data

US 2013/0032728 A1 Feb. 7, 2013

(30) Foreign Application Priority Data

Aug. 5, 2011 (JP) .................................. 2011-171824

(51) Int. Cl.
*G01J 1/42* (2006.01)
*G01T 1/00* (2006.01)
*G01N 23/083* (2006.01)

(52) U.S. Cl.
CPC ...... *G01N 23/083* (2013.01); *G01N 2223/3307* (2013.01)
USPC .......................... 250/394; 250/336.1; 250/307

(58) Field of Classification Search
CPC ..................... G01N 23/083; G01N 2223/3307
USPC ....................... 250/394, 336.1, 307
See application file for complete search history.

(56) References Cited

U.S. PATENT DOCUMENTS

| 5,391,866 A | * | 2/1995 | Hoshino et al. | ............ | 250/201.2 |
| 2009/0224151 A1 | * | 9/2009 | Hatakeyama et al. | ......... | 250/307 |
| 2010/0322494 A1 | * | 12/2010 | Fauver et al. | .................. | 382/131 |

FOREIGN PATENT DOCUMENTS

| JP | 2000050063 | | 2/2000 |
| JP | 2003046862 A | * | 2/2003 |
| JP | 2008152011 A | * | 7/2008 |
| JP | 2010004105 | | 1/2010 |

* cited by examiner

*Primary Examiner* — David Porta
*Assistant Examiner* — Abra Fein
(74) *Attorney, Agent, or Firm* — Adams & Wilks

(57) ABSTRACT

A transmission X-ray analyzer for detecting a transmission X-ray image of a sample that moves relatively in a predetermined scanning direction includes; a time delay and integration (TDI) sensor including a plurality of stages of line sensors including the plurality of two-dimensionally arranged image pickup devices arranged in a direction perpendicular to the predetermined scanning direction, being configured to transfer charge accumulated in one line sensor to an adjacent subsequent line sensor; a shield unit for shielding a part of the image of light entering the TDI sensor by moving back and forth in the predetermined scanning direction, the shield unit being disposed between the TDI sensor and the sample; and a shield unit position control unit for controlling a position of the shield unit so as to shield a predetermined number of stages of line sensors among the plurality of stages of line sensors.

10 Claims, 5 Drawing Sheets

TRANSMISSION X-RAY ANALYZER AND TRANSMISSION X-RAY ANALYSIS METHOD

BACKGROUND OF THE INVENTION

1. Field of the Invention

The present invention relates to a transmission X-ray analyzer and a transmission X-ray analysis method, which are capable of measuring a transmission X-ray output from a sample through use of a time delay and integration (TDI) sensor.

2. Description of the Related Art

Conventionally, a foreign matter in a sample and density unevenness of elements have been detected by X-ray transmission imaging. As a method of the X-ray transmission imaging, there is known a method of converting a transmission X-ray output from a sample into fluorescent light through a fluorescent screen or the like, and detecting the fluorescent light through use of image pickup devices (charge coupled devices (CCDs)). As a detection method using CCDs, there is a method of scanning a sample to obtain linear images successively through use of a line sensor having a plurality of image pickup devices arranged in one direction, thereby obtaining a two-dimensionally image of the sample.

By the way, when the movement speed of a sample in a scanning direction increases, the time period of accumulation of charge in the line sensor becomes shorter, and in the case where the sensitivity of the line sensor is low, an S/N ratio decreases. For this reason, a time delay and integration (TDI) sensor has been used, in which a plurality of (stages of) line sensors are arranged in parallel in the scanning direction and charge accumulated in one line sensor is transferred to an adjacent subsequent line sensor. In the TDI sensor, the charge accumulated in a line sensor of the first stage is transferred to a line sensor of the second stage. In a line sensor of the second stage, the charge transferred from the line sensor of the first stage is added to the charge accumulated when the line sensor of the second stage receives light, and the resultant charge is transferred to a line sensor of the third stage. Thus, charge transferred from a line sensor of the previous stage is added sequentially to each line sensor, and accumulated charge transferred to a line sensor of the last stage is output.

Accordingly, in the TDI sensor, in the case where the number of stages is T, charge which is T times as large as that of a single line sensor is accumulated, and a contrast becomes T times as high as that of a single line sensor. Further, noise is reduced, measurement can be performed at high speed, and an S/N ratio increases.

On the other hand, due to high sensitivity, the TDI sensor has problems in that a defect (artifact) appears in a detected image due to a change in a received light amount, and that noise is superimposed at a time of rising or falling of a vertical transfer clock for charge transfer. Therefore, a technology of controlling the number of integration stages of the TDI sensor through use of an electric circuit has been developed (Japanese Patent Application Laid-open Nos. 2000-50063 and 2010-4105).

Further, according to the study conducted by the inventors of the present invention, in the case of using the TDI sensor for a transmission X-ray analysis, as the number of integration stages of the TDI sensor increases, a depth of field decreases. In the case of a thick sample, only a part of the sample in a depth direction is focused to be formed as an image, and the remaining part is not formed as an image. Therefore, there is a problem in that the entire sample cannot be grasped.

According to the technology described in Japanese Patent Application Laid-open Nos. 2000-50063 and 2010-4105, however, the number of integration stages of the TDI sensor is controlled through use of an electric circuit, and it is necessary to manufacture a TDI sensor having a dedicated integrated circuit (IC) such as an application-specific integrated circuit (ASIC) and to change arithmetic software of a TDI sensor. Thus, a general-purpose TDI sensor cannot be used, leading to an increase in cost. Further, in the case where the number of integration stages is set on an electric circuit and arithmetic software as in the technology described in Japanese Patent Application Laid-open Nos. 2000-50063 and 2010-4105, it is difficult for a measurer to freely adjust the number of integration stages T depending upon the thickness of a sample and the kind thereof.

SUMMARY OF THE INVENTION

The present invention has been made to solve the above-mentioned problems, and to provide an X-ray analyzer and an X-ray analysis method, which are capable of easily adjusting the number of integration stages of a TDI sensor in a wide range.

In order to achieve the above-mentioned object, according to an exemplary embodiment of the present invention, there is provided a transmission X-ray analyzer for detecting a transmission X-ray image of a sample that moves relatively in a predetermined scanning direction, the transmission X-ray analyzer including: a time delay and integration (TDI) sensor including a plurality of two-dimensionally arranged image pickup devices for reading charge generated when an image derived from the transmission X-ray image is subjected to photoelectric conversion, the TDI sensor including a plurality of stages of line sensors including the plurality of two-dimensionally arranged image pickup devices arranged in a direction perpendicular to the predetermined scanning direction, the plurality of stages of line sensors being arranged in the predetermined scanning direction, the TDI sensor being configured to transfer charge accumulated in one line sensor to an adjacent subsequent line sensor; shield means for shielding a part of the image of light entering the TDI sensor by moving back and forth in the predetermined scanning direction, the shield means being disposed between the TDI sensor and the sample; and shield means position control means for controlling a position of the shield means so as to shield a predetermined number of stages of line sensors among the plurality of stages of line sensors.

In the above-mentioned transmission X-ray analyzer, it is only necessary that the number of integration stages of the TDI sensor be adjusted physically through use of the shield means. Therefore, it is not necessary to manufacture a dedicated TDI sensor for controlling the number of integration stages through use of an electric circuit and arithmetic software, and a cost can be reduced through use of a general-purpose TDI sensor. Further, in the case of adjusting the number of integration stages through use of a dedicated TDI sensor, it is difficult for a measurer to freely adjust the number of integration stages. However, in the present invention, it is only necessary that the movement amount of the shield means be adjusted physically, and hence, the number of integration stages of the TDI sensor can be adjusted freely.

Further, in the case of using the TDI sensor for a transmission X-ray analysis, as the number of integration stages of the TDI sensor increases, a depth of field decreases. In the case of a thick sample, only a part of the sample in a depth direction is focused to be formed as an image, and the remaining part is not formed as an image. Therefore, the entire sample may not be grasped. In the transmission X-ray analyzer of the present invention, the measurer can freely adjust the number of integration stages, and hence, the range in which a thick sample is focused can be set to be the largest range.

According to an exemplary embodiment of the present invention, there is provided a transmission X-ray analysis method of detecting a transmission X-ray image of a sample that moves relatively in a predetermined scanning direction, the transmission X-ray analysis method including: transferring charge accumulated in one line sensor to an adjacent subsequent line sensor through use of a time delay and integration (TDI) sensor including a plurality of two-dimensionally arranged image pickup devices for reading charge generated when an image derived from the transmission X-ray image is subjected to photoelectric conversion, the TDI sensor including a plurality of stages of line sensors including the plurality of two-dimensionally arranged image pickup devices arranged in a direction perpendicular to the predetermined scanning direction, the plurality of stages of line sensors being arranged in the predetermined scanning direction; and shielding, by shield means disposed between the TDI sensor and the sample, a predetermined arbitrary number of stages of line sensors among the plurality of stages of line sensors.

According to the present invention, when the transmission X-ray image of the sample is detected through use of the TDI sensor, the number of integration stages of the TDI sensor can be adjusted easily in a wide range.

DETAILED DESCRIPTION OF THE PREFERRED EMBODIMENT

Hereinafter, an embodiment of the present invention is described with reference to the drawings.

Figure 1:
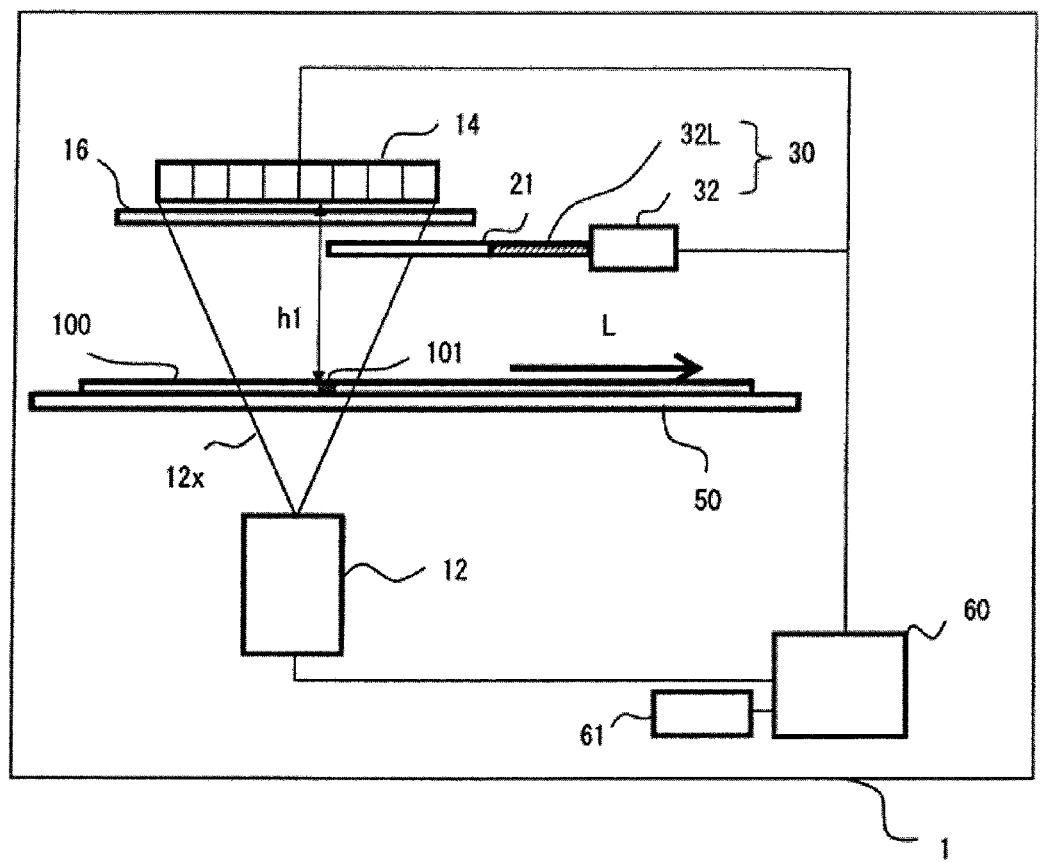
FIG. 1 is a block diagram illustrating a configuration of a transmission X-ray analyzer according to an embodiment of the present invention.

FIG. 1 is a block diagram illustrating a configuration of a transmission X-ray analyzer 1 according to the embodiment of the present invention.

The transmission X-ray analyzer 1 includes: an X-ray source 12; a time delay and integration (TDI) sensor 14; a fluorescent screen 16 that is disposed between the TDI sensor 14 and a sample 100 and configured to convert a transmission X-ray 12x from the sample 100 into fluorescent light (visible light image); a shield plate (shield means) 21 that is disposed below the fluorescent screen 16 and configured to shield a part of an image of visible light entering the TDI sensor 14; shield plate movement means 30 for moving the shield plate 21 back and forth relative to the TDI sensor 14; and shield means position control means 60 (position control portion) for controlling the position of the shield plate 21.

Herein, the X-ray source 12 is disposed below the sample 100. An X-ray is emitted upward from the X-ray source 12 to pass through the sample 100 and is then converted into a visible light image through a fluorescent screen 16. Then, the visible light image is received by the TDI sensor 14 disposed above the sample 100. Note that, the sample 100 is, for example, a continuous strip of a lithium cobaltate electrode plate to be used for a positive electrode of a lithium ion battery, and placed on a belt conveyer 50 so as to move in a scanning direction L (from left to right in FIG. 1). An X-ray is constantly emitted from the X-ray source 12 so as to continuously analyze the moving sample 100 using the X-ray.

The shield means position control means (position control portion) 60 is implemented by a computer, which includes a CPU, a ROM, a RAM, and the like. The shield means position control means 60 is capable of executing predetermined computer programs, and also performs the overall processing such as the irradiation of X-rays from the X-ray source 12, reception of light of a visible light image by the TDI sensor 14, and output processing.

Further, the transmission X-ray analyzer 1 is configured to detect a foreign matter 101 (e.g., Fe) in the sample 100.

The X-ray source 12 includes a predetermined X-ray tubular bulb. The X-ray tubular bulb, for example, emits as a primary X-ray an X-ray, which is generated by the fact that thermoelectrons generated from a filament (positive electrode) of the tubular bulb are accelerated by a voltage applied between the filament (positive electrode) and a target (negative electrode) to thereby smash against the target (tungsten (W), molybdenum (Mo), chromium (Cr), or the like), from a window of a beryllium foil or the like.

Figure 2:
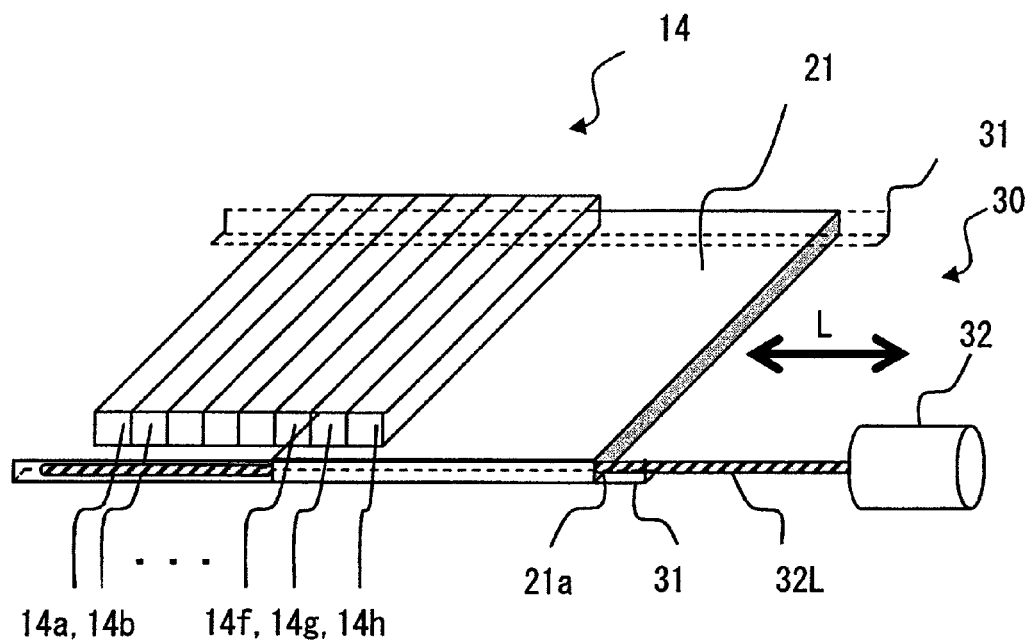
FIG. 2 is a perspective view illustrating a configuration of a shield plate.

The TDI sensor 14 has a configuration in which a plurality of image pickup devices (charge coupled devices (CCDs)) are arranged in a two-dimensionally array. As illustrated in FIG. 2, the TDI sensor 14 has a configuration in which a plurality of stages (eight stages in the example of FIG. 2; however, actually, several hundred to several thousand stages) of line sensors 14a to 14h having image pickup devices arranged in a direction perpendicular to the scanning direction L are arranged in the scanning direction L.

As illustrated in FIG. 2, the shield plate 21 is formed into a rectangular shape, and two sides of the shield plate 21 are disposed perpendicularly to the scanning direction L and in parallel to the line sensors 14a to 14h. Two side edges of the shield plate 21 disposed along the scanning direction L are placed on a pair of rails 31 having an L-shaped cross-section so as to be interposed between the rails 31. Accordingly, the shield plate 21 can move back and forth in the scanning direction L along the rails 31. Further, one side of the shield plate 21 has a through-hole 21a formed therein in the scanning direction L, and the inside of the through-hole 21a is threaded. A feed screw 32L rotationally driven by a stepping motor 32 is threadedly engaged with the through-hole 21a, and the rotation of the stepping motor 32 allows the shield plate 21 to move back and forth in the scanning direction L along the rails 31.

The rails 31, the stepping motor 32, and the feed screw 32L are collectively referred to as the shield plate movement means 30. Further, the shield means position control means 60 described later adjusts the rotation amount of the stepping motor 32 to control the feed amount of the feed screw 32L, thereby controlling the movement amount of the shield plate 21 in the L direction.

As described above, when the shield plate 21 moves in the scanning direction L, apart of the line sensors 14a to 14h is shielded, and the number of stages of time delay and integration by the TDI sensor 14 is physically adjusted, as described later.

Note that, the configuration of the shield plate movement means 30 is not limited to the above-mentioned configuration, nor is the configuration of the shield plate 21 limited to the above-mentioned configuration. Further, as the shield plate 21, for example, a sheet of tungsten or molybdenum (for example, thickness: about 0.5 mm) can be used.

Next, an example of a method of time delay and integration processing by the TDI sensor 14 is described with reference to FIGS. 3A and 3B. Herein, as illustrated in FIG. 2, the TDI sensor 14 includes the plurality of stages (eight stages) of line sensors 14a to 14h.

Figure 3A:
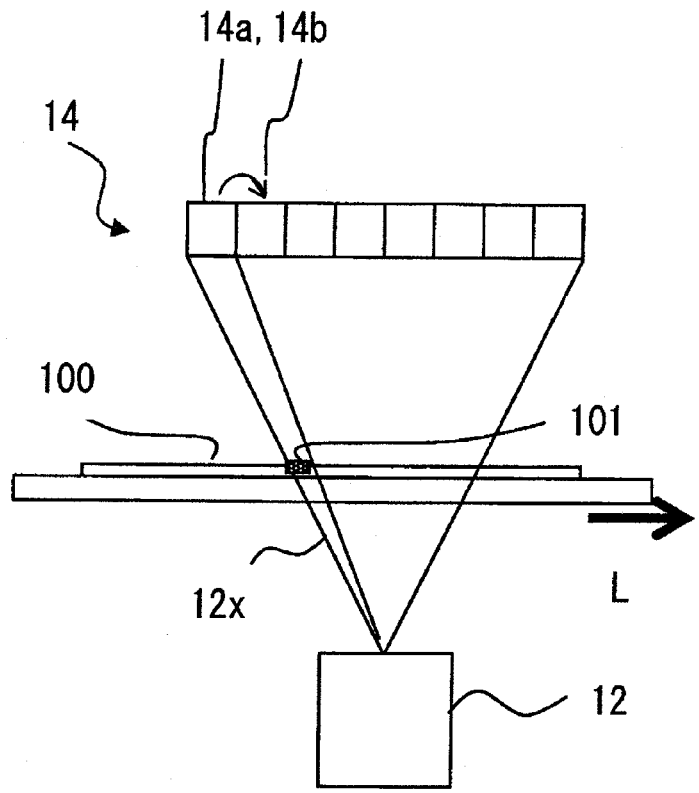
FIGS. 3A and 3B are diagrams illustrating an example of a method of time delay and integration processing through use of a TDI sensor.
Figure 3B:
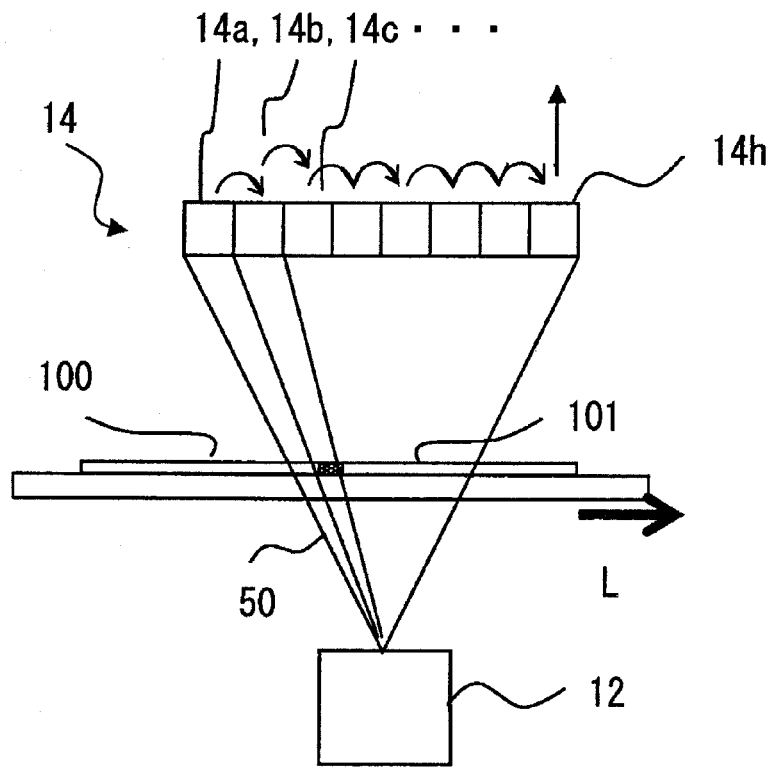

Assuming that the foreign matter 101 in the sample 100 enters a light-receiving region of the line sensor 14a of the first stage, charge accumulated in the line sensor 14a is transferred to the line sensor 14b of the second stage (FIG. 3A). Next, assuming that the foreign matter 101 moves in the scanning direction L and enters a light-receiving region of the line sensor 14b of the second stage, charge is accumulated in the line sensor 14b (FIG. 3B).

In the line sensor 14b of the second stage, the charge transferred from the line sensor 14a of the first stage is added to the charge accumulated when the line sensor 14b of the second stage receives light, and the resultant charge is transferred to the line sensor 14c of the third stage. Thus, charge transferred from a line sensor of the previous stage is added sequentially to each of the line sensors 14a to 14h, and accumulated charge transferred to the line sensor 14h of the last stage is output. Then, the sample 100 moving in the scanning direction L is subjected to a line analysis continuously, with the result that two-dimensionally image data of the sample 100 is obtained continuously.

Accordingly, in the TDI sensor 14, in the case where the number of stages is T, charge which is T times as large as that of a single line sensor is accumulated, and a contrast becomes T times as high as that of a single line sensor. Further, noise is reduced, measurement can be performed at high speed, and an S/N ratio increases.

Note that, as the configuration and operation of the TDI sensor 14, publicly-known configuration and operation can be used.

Figure 4:
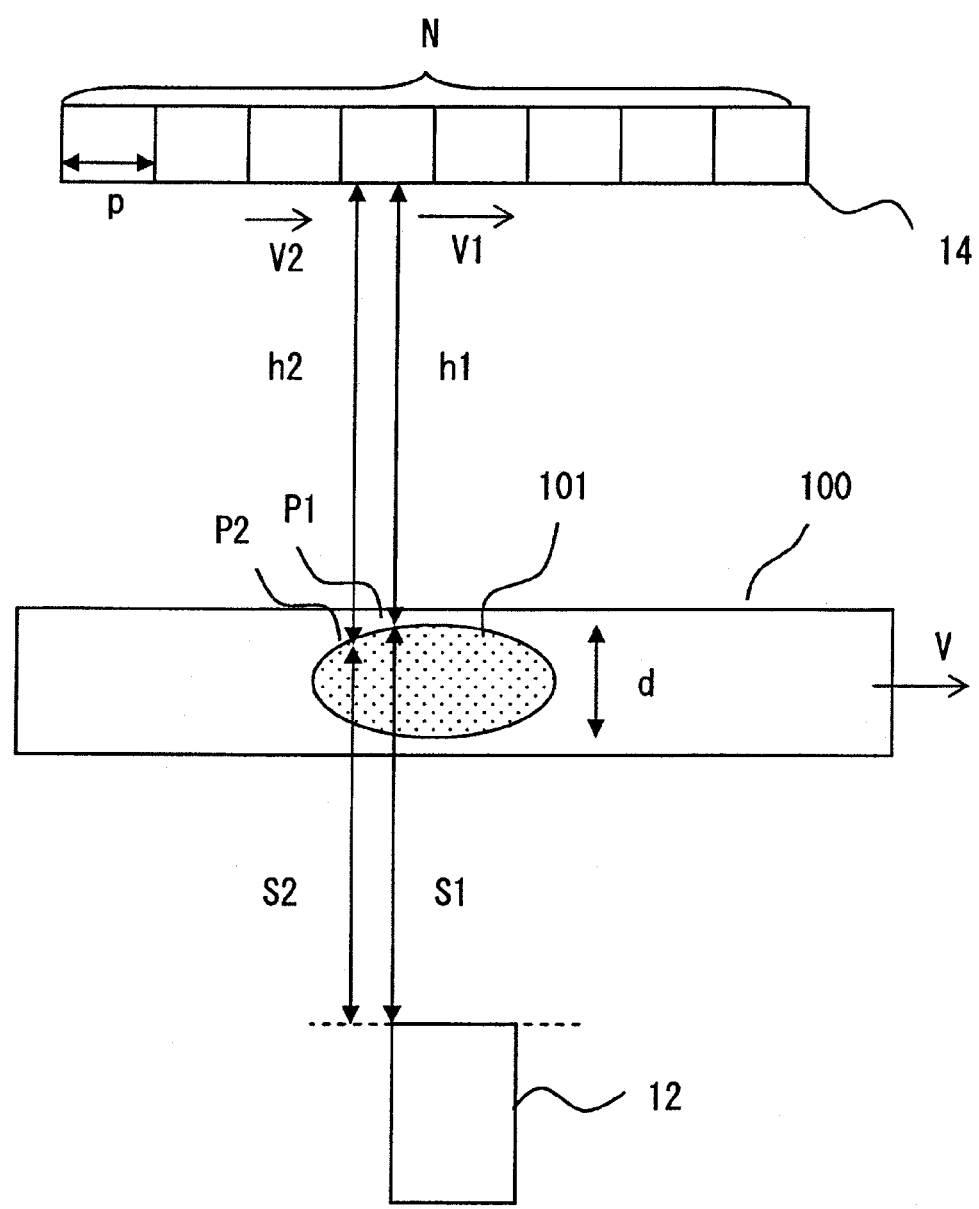
FIG. 4 is a diagram illustrating a state in which a depth of field decreases depending upon the position of an object to be analyzed in a depth direction in the case of using the TDI sensor for a transmission X-ray analysis.

By the way, as illustrated in FIG. 4, in the case of using the TDI sensor 14 for a transmission X-ray analysis, when a thickness d of the foreign matter 101 in the sample 100 to be analyzed increases, distances h1, h2 between the TDI sensor 14 and the foreign matter 101 vary depending upon positions P1, P2 of the foreign matter 101 in a depth direction. At this time, as a number N of integration stages of the TDI sensor 14 increases, a depth of field decreases. Only the position P1 of the thick foreign matter 101 is focused to be formed as an image, and the position P2 is not formed as an image. Therefore, the entire sample cannot be grasped. This is described with reference to FIG. 4. First, it is assumed that the distances from the X-ray source 12 to the positions P1 and P2 are respectively S1 and S2, and a scanning (movement) speed of the sample 100 (foreign matter 101) in the scanning direction L is V.

In this case, a movement speed V1 of a shadow cast onto the TDI sensor 14 by the position P1 becomes V×(S1+h1)/h1. Similarly, a movement speed V2 of a shadow cast onto the TDI sensor 14 by the position P2 becomes V×(S2+h2)/h2. On the other hand, the scanning speed V can be set to be only one value relative to the positions P1 and P2, and hence, assuming that V1=V, the movement speed V1 of the shadow cast onto the TDI sensor 14 by the position P1 is equal to the scanning speed V of the sample 100. Consequently, the shadow of the position P1 is formed as an image. In contrast, the movement speed V2 of the shadow cast onto the TDI sensor 14 by the position P2 is not equal to the scanning speed V, and hence, the shadow of the position P2 blurs over a plurality of stages of the TDI sensor 14. In particular, this problem becomes conspicuous in the case where the foreign matter 101 to be detected enters not only the surface of the sample 100 but also a portion in the depth direction, or in the case where the thickness of the foreign matter 101 exceeds about 2 mm.

Herein, a number NE of stages in which the shadow of the position P2 blurs on the TDI sensor 14 is represented by N×(V2−V1)/V1, which is proportional to the number N of integration stages of the TDI sensor 14. Thus, the range in which the foreign matter 101 having a variable depth depending upon the position is focused can be enlarged by decreasing the number N of integration stages.

Figure 5:
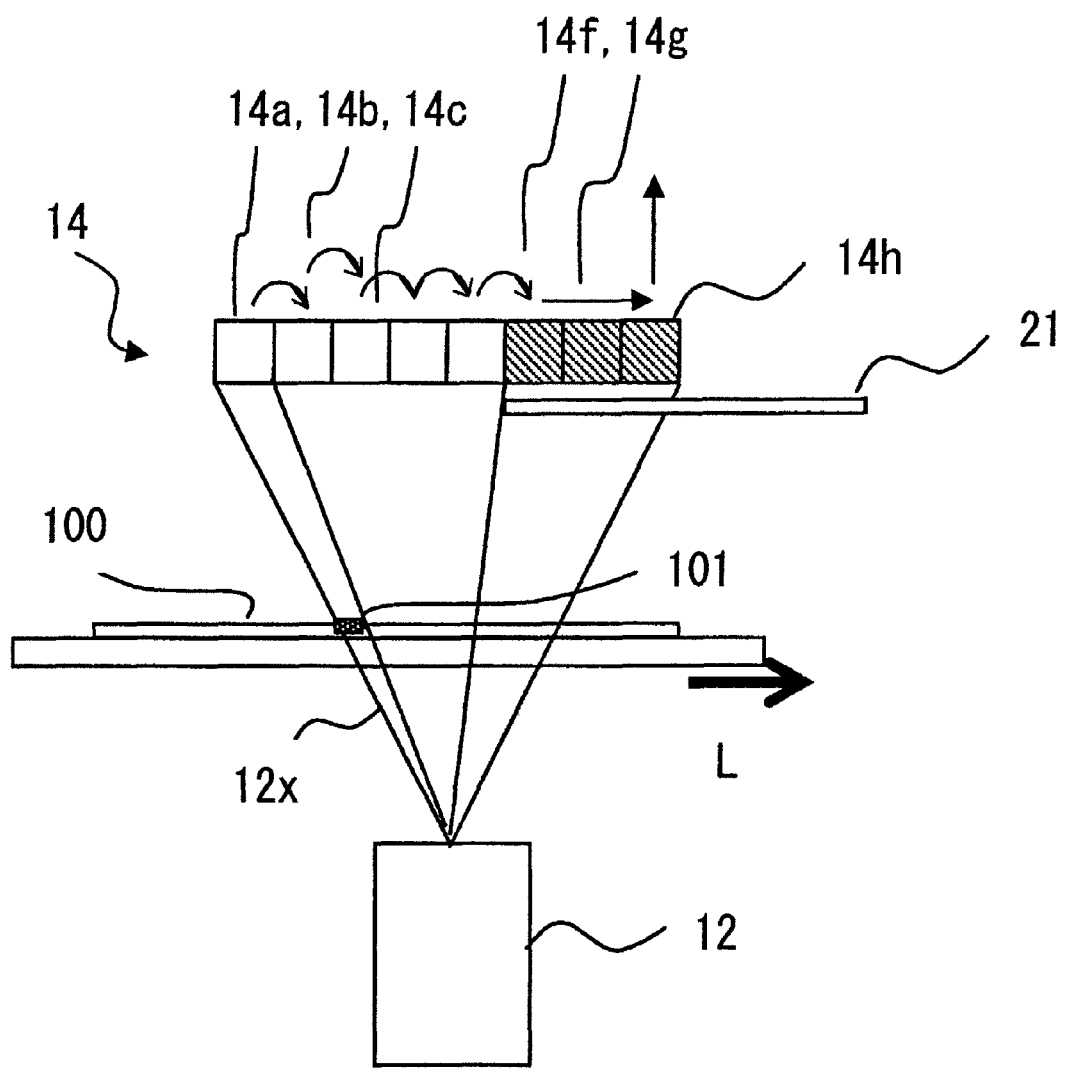
FIG. 5 is a diagram illustrating a method of moving the shield plate in an L direction to reduce the number of stages in which time delay and integration is performed, to thereby increase the depth of field of the TDI sensor.

More specifically, as illustrated in FIG. 5, the number of stages in which time delay and integration is performed is reduced and a depth of field of the TDI sensor 14 is increased by moving the shield plate 21 in the scanning direction L to shield a part (in the example of FIG. 5, three line sensors 14f to 14h on the latter stage side) of the line sensors 14a to 14h.

In the case of using the shield plate 21, a general-purpose TDI sensor 14 can be used. More specifically, in the same way as in FIGS. 3A and 3B, the charge transferred from the line sensor of the previous stage is added sequentially to each of the line sensors 14a to 14h, and accumulated charge transferred to the line sensor 14h of the last stage is output. However, in the line sensors 14f to 14h which cannot receive light of an image as being shielded through use of the shield plate 21, charge of the line sensors 14f to 14h themselves is not accumulated, and hence, the accumulated charge transferred sequentially from the line sensors 14a to 14e is transferred directly to the line sensors 14f to 14h sequentially and output from the line sensor 14h of the last stage. Thus, a preselected arbitrary number of integration stages of the TDI sensor 14 can be reduced (five stages in the example of FIG. 5).

As described above, it is only necessary that the number of stages of the TDI sensor 14 be adjusted physically through use of the shield plate 21. Therefore, it is not necessary to manufacture a dedicated TDI sensor as in the case of controlling the number of integration stages of a TDI sensor through use of its electric circuit and arithmetic software, and a cost can be reduced through use of a general-purpose TDI sensor. Further, in the case of adjusting the number of integration stages through use of a dedicated TDI sensor, it is difficult for a measurer to freely adjust the number of integration stages. However, in the present invention, it is only necessary that the movement amount of the shield plate 21 be adjusted physically, and hence, the number of integration stages of the TDI sensor can be adjusted freely.

For example, in the case of analyzing a thin sample, it is only necessary that the number of stages of the TDI sensor 14 be increased, and in the case of analyzing a thick sample, it is only necessary that the number of stages of the TDI sensor 14 be decreased. The number of stages of the TDI sensor 14 can be adjusted, for example, by connecting an input device 61 such as a keyboard to the computer (shield means position control means) 60 and allowing the measurer to input arbitrary movement amount of the shield plate 21 (or the number of stages of the TDI sensor 14 in accordance with the movement amount) through the input device 61. The shield means position control means 60 controls the rotation of the stepping motor 32 based on information input by the measurer and adjusts the movement amount of the shield plate 21.

It is to be understood that the present invention is not limited to the embodiment described above, and that the scope of the present invention encompasses various modifications and equivalents included in the idea and the scope of the present invention.

What is claimed is:

1. A transmission X-ray analyzer for detecting a transmission X-ray image of a sample that moves relatively in a predetermined scanning direction, the transmission X-ray analyzer comprising:
a time delay and integration (TDI) sensor comprising a plurality of two-dimensionally arranged image pickup devices for reading charge generated when an image derived from the transmission X-ray image is subjected to photoelectric conversion,
the TDI sensor comprising a plurality of stages of line sensors including the plurality of two-dimensionally arranged image pickup devices arranged in a direction perpendicular to the predetermined scanning direction, the plurality of stages of line sensors being arranged in the predetermined scanning direction, and
the TDI sensor being configured to transfer charge accumulated in one line sensor to an adjacent subsequent line sensor;
shielding means for shielding an image of light entering an arbitrary number of stages of the TDI sensor by moving back and forth in the predetermined scanning direction, the shielding means being disposed between the TDI sensor and the sample; and
position control means for controlling a position of the shielding means so as to shield an arbitrary number of stages of line sensors among the plurality of stages of line sensors.

2. A transmission X-ray analysis method of detecting a transmission X-ray image of a sample that moves relatively in a predetermined scanning direction, the transmission X-ray analysis method comprising:
transferring charge accumulated in one line sensor to an adjacent subsequent line sensor through use of a time delay and integration (TDI) sensor comprising a plurality of two-dimensionally arranged image pickup devices for reading charge generated when an image derived from the transmission X-ray image is subjected to photoelectric conversion,
the TDI sensor comprising a plurality of stages of line sensors including the plurality of two-dimensionally arranged image pickup devices arranged in a direction perpendicular to the predetermined scanning direction, the plurality of stages of line sensors being arranged in the predetermined scanning direction; and
shielding, by shield means movably disposed between the TDI sensor and the sample, an image of light entering an arbitrary number of stages of line sensors among the plurality of stages of line sensors.

3. A transmission X-ray analyzer for detecting a transmission X-ray image of a sample moving in a predetermined scanning direction, the transmission X-ray analyzer comprising:
a time delay and integration (TDI) sensor comprising plural stages of line sensors arranged in the predetermined scanning direction and configured to accumulate charge in accordance with a light image derived from a transmission X-ray transmitted through the moving sample, the TDI sensor being configured to sequentially transfer charge accumulated in one line sensor to an adjacent subsequent line sensor;
a shield disposed between the TDI sensor and the sample, the shield being movable back and forth in the predetermined scanning direction to selectively shield an arbitrary number of stages of line sensors from receiving a part of the light image; and
a position control portion that controls movement of the shield to a position in which it shields an arbitrary number of stages of line sensors from among the plural stages of line sensors thereby adjusting the number of stages of the TDI sensor.

4. A transmission X-ray analyzer according to claim 3; wherein the shield comprises a shield plate.

5. A transmission X-ray analyzer according to claim 3; wherein the position control portion comprises a motor connected to move the shield back and forth in the predetermined scanning direction, and an input device for inputting information to control operation of the motor.

6. A transmission X-ray analyzer according to claim 5; wherein the position control portion includes a feed screw threadedly engaged with a threaded hole in the shield, and the motor comprises a rotary stepping motor connected to rotationally drive the feed screw to move and position the shield.

7. A transmission X-ray analyzer according to claim 6; wherein the shield is movable along rails that extend parallel to the predetermined scanning direction.

8. A transmission X-ray analyzer according to claim 7; wherein the shield comprises a shield plate having opposed side edges movable along the rails.

9. A transmission X-ray analyzer according to claim 3; further comprising means disposed between the TDI sensor and shield for converting the transmission X-ray into a light image which is incident on the TDI sensor.

10. A transmission X-ray analyzer according to claim 9; wherein the means for converting comprises a fluorescent screen.

* * * * *